United States Patent
Mestad et al.

(10) Patent No.: US 8,764,451 B2
(45) Date of Patent: Jul. 1, 2014

(54) DEVICE FOR SIMULATING VARIABLE LUNG COMPLIANCE

(75) Inventors: Einar Mestad, Hundvag (NO); Einar Egelandsdal, Stavanger (NO); Oystein Gomo, Hundvag (NO)

(73) Assignee: Laerdal Medical AS, Stavanger (NO)

( * ) Notice: Subject to any disclaimer, the term of this patent is extended or adjusted under 35 U.S.C. 154(b) by 944 days.

(21) Appl. No.: 12/810,034

(22) PCT Filed: Jan. 9, 2009

(86) PCT No.: PCT/NO2009/000011
§ 371 (c)(1),
(2), (4) Date: Jun. 22, 2010

(87) PCT Pub. No.: WO2009/088304
PCT Pub. Date: Jul. 16, 2009

(65) Prior Publication Data
US 2010/0285439 A1   Nov. 11, 2010
US 2012/0034588 A9   Feb. 9, 2012

(30) Foreign Application Priority Data
Jan. 11, 2008 (NO) .................................. 2008 0206

(51) Int. Cl.
*G09B 23/28* (2006.01)
*A61B 5/00* (2006.01)
*G06F 19/00* (2011.01)

(52) U.S. Cl.
CPC .............. *G09B 23/28* (2013.01); *A61B 5/0002* (2013.01); *G06F 19/3406* (2013.01)
USPC ............ 434/272; 434/267; 434/262; 600/301

(58) Field of Classification Search
USPC ............... 434/262, 272; 128/200.24; 600/301
See application file for complete search history.

(56) References Cited

U.S. PATENT DOCUMENTS

| | | | |
|---|---|---|---|
| 2,772,664 A | | 12/1956 | Jones |
| 2,999,495 A | * | 9/1961 | Shipley .......................... 600/541 |
| 3,363,260 A | * | 1/1968 | Garbe ............................ 600/541 |

(Continued)

FOREIGN PATENT DOCUMENTS

| | | |
|---|---|---|
| DE | 3049583 A1 | 7/1982 |
| GB | 1293633 A | 10/1972 |
| WO | WO-2005/032327 A2 | 4/2005 |

OTHER PUBLICATIONS

Toll, Anders / MRo, "International Search Report", for PCT/NO2009/000011 as mailed Apr. 2, 2009, 4 pages.

*Primary Examiner* — Xuan Thai
*Assistant Examiner* — Banafsheh Hadizonooz
(74) *Attorney, Agent, or Firm* — Winstead PC

(57) ABSTRACT

Device for simulating variable lung compliance, comprising a structure having two main components (3, 4) between which an artificial lung (1) is situated, the main components (3, 4) being adapted to be moved away from each other by the lung (1) when the lung is inflated and are adapted to move towards one another to force air out of the lung (1) in an exhalation phase; and a biasing means (17, 18) acting to provide a force that acts to move the two main parts (3, 4) towards one another. The biasing means comprises at least one spring (17, 18), which is selectively attachable to impose the force, upon actuation by a spring holding mechanism (22, 32).

10 Claims, 6 Drawing Sheets

Lung System

(56) References Cited

U.S. PATENT DOCUMENTS

Figure 4:
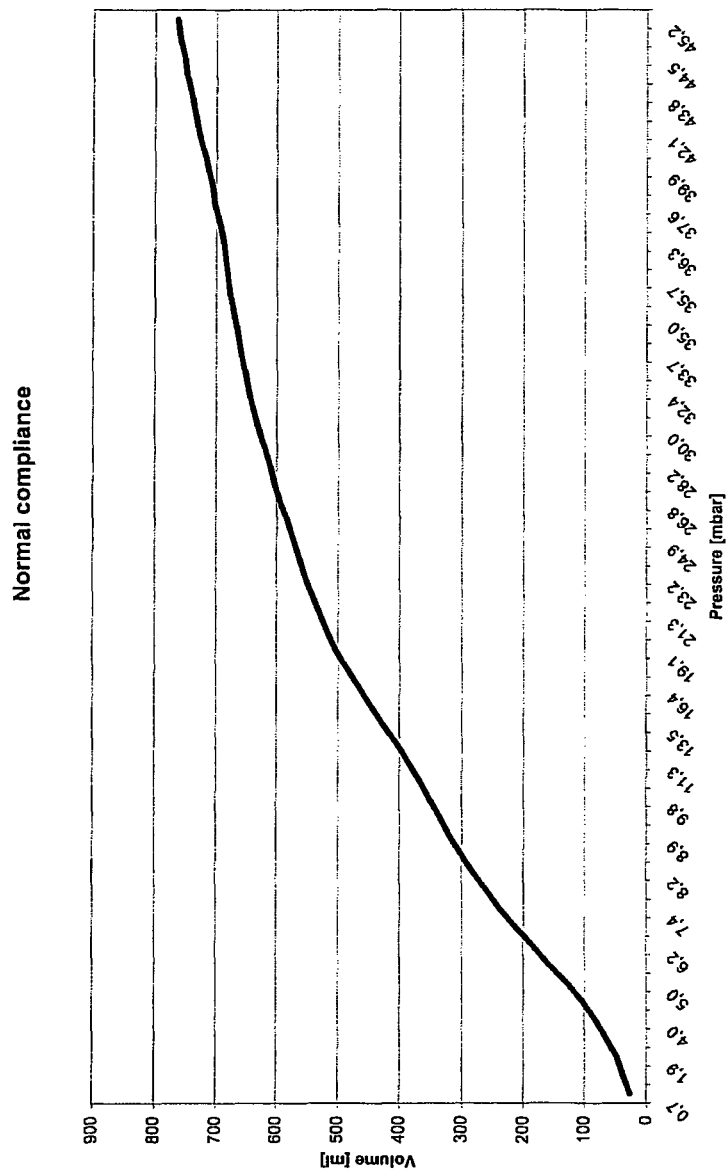
Figure 5:
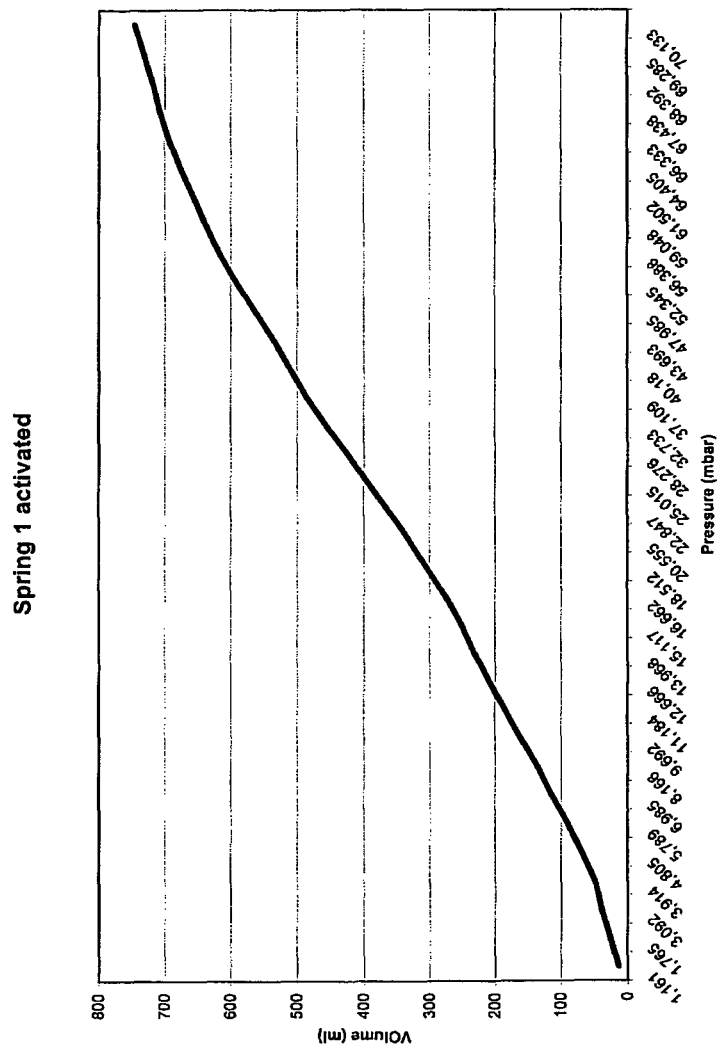
Figure 6:
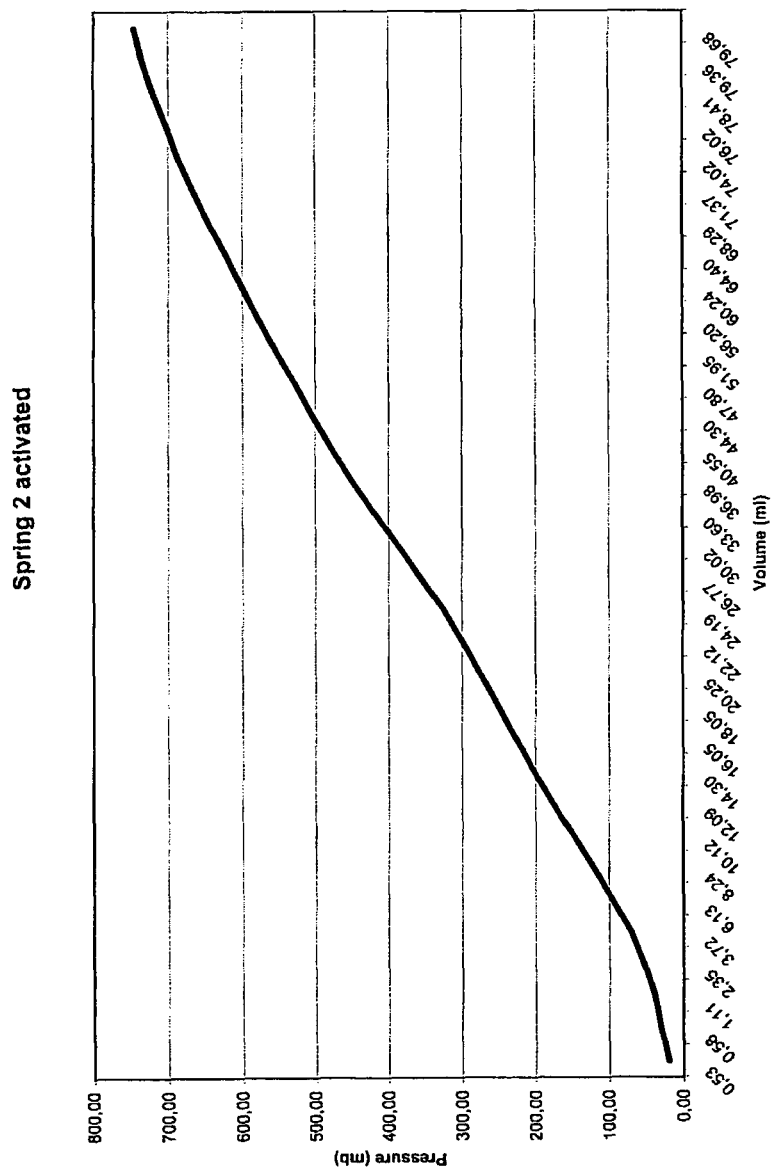
Figure 7:
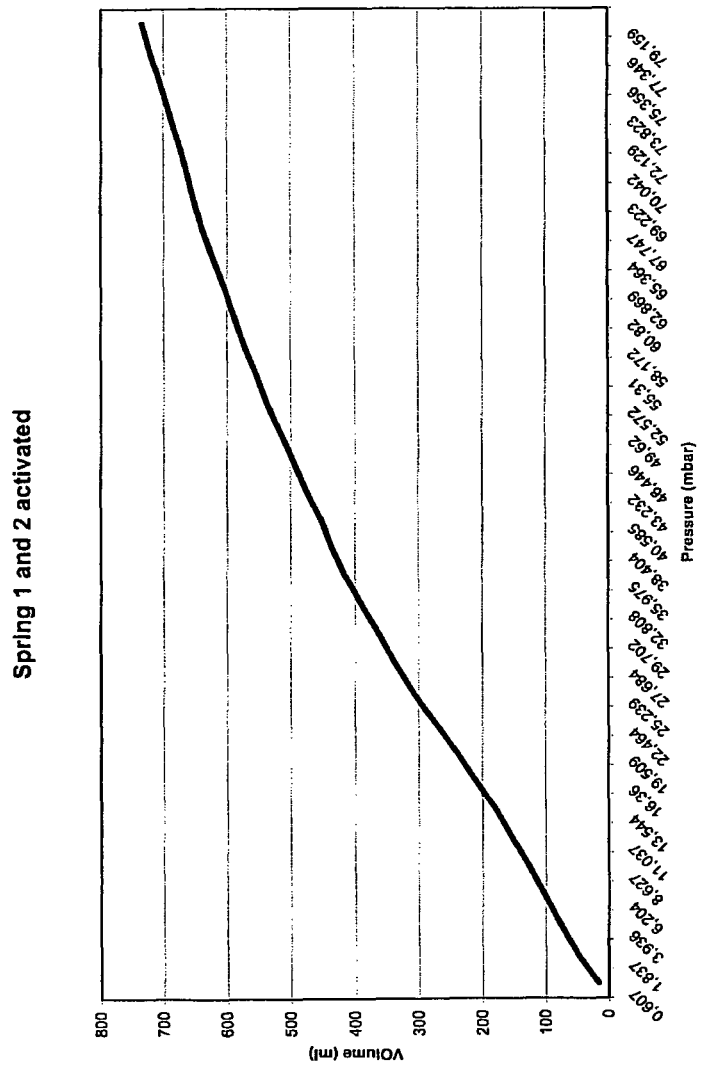

| | | |
|---|---|---|
| 3,657,925 A | 4/1972 | Gross |
| 3,736,362 A | 5/1973 | Laerdal |
| 3,808,706 A * | 5/1974 | Mosley et al. ............... 73/865.9 |
| RE29,317 E | 7/1977 | Mosley et al. |
| 4,240,291 A | 12/1980 | Andersson et al. |
| 4,430,893 A * | 2/1984 | Barkalow ...................... 73/168 |
| 5,772,443 A * | 6/1998 | Lampotang et al. .......... 434/272 |
| 5,873,731 A | 2/1999 | Prendergast |
| 5,941,710 A * | 8/1999 | Lampotang et al. .......... 434/272 |
| 6,503,087 B1 * | 1/2003 | Eggert et al. .................. 434/262 |
| 7,316,568 B2 * | 1/2008 | Gordon et al. ................ 434/262 |
| 7,857,625 B2 * | 12/2010 | Gomo ........................... 434/267 |

\* cited by examiner

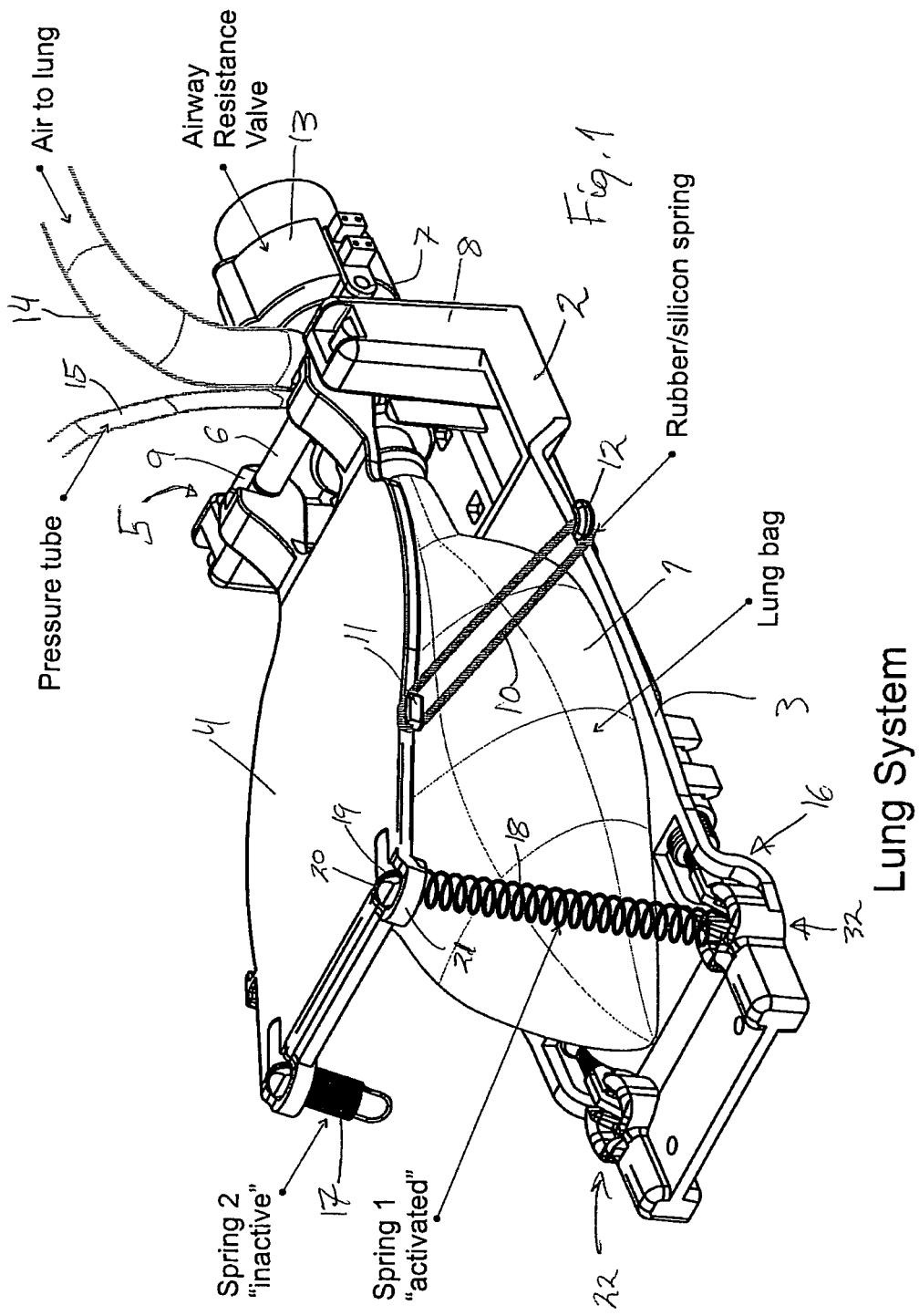

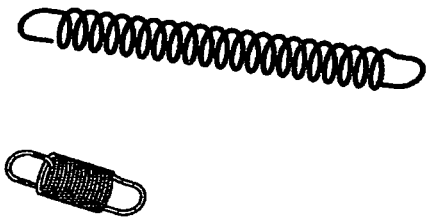
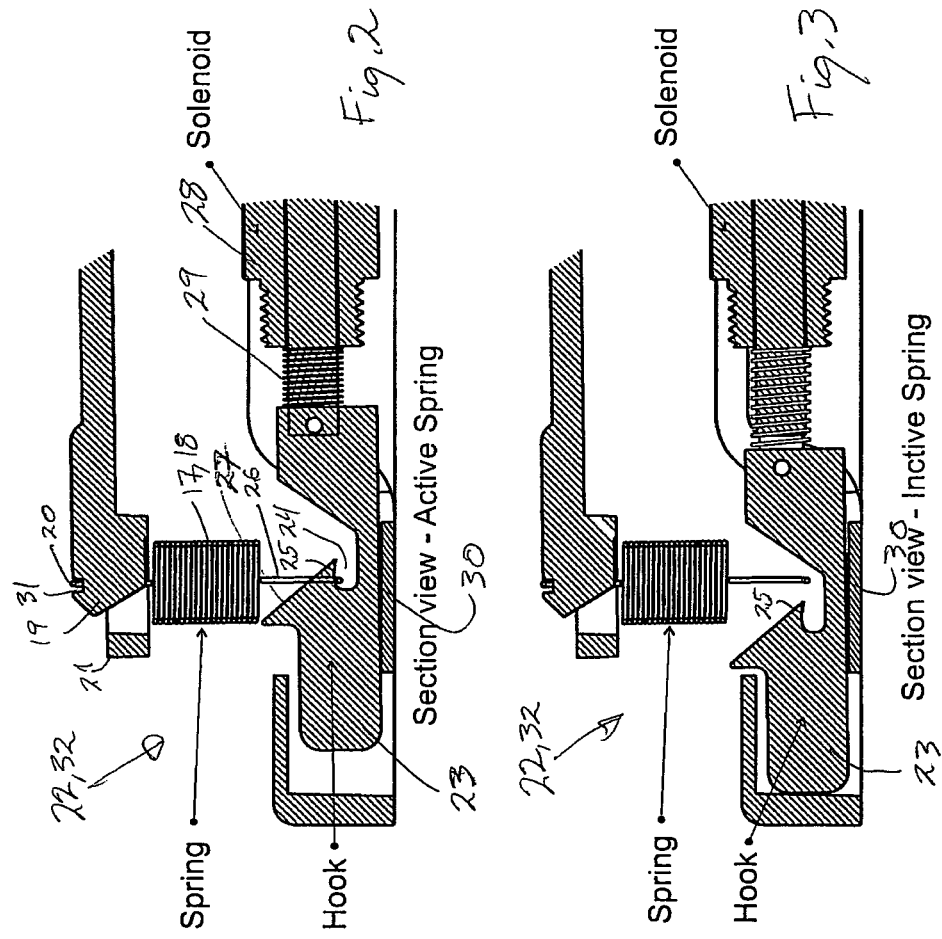
Fig. 2 Section view - Active Spring
Fig. 3 Section view - Inactive Spring

DEVICE FOR SIMULATING VARIABLE LUNG COMPLIANCE

CROSS REFERENCE TO RELATED APPLICATIONS

This application is a U.S. National Stage filing of International Application Number PCT/NO2009/000011, filed on Jan. 9, 2009. PCT/NO2009/000011 claims priority from U.S. Provisional Patent Application No. 61/006,439, filed on Jan. 14, 2008. PCT/NO2009/000011 and U.S. Provisional Patent Application No. 61/006,439 are incorporated herein by reference.

The present invention relates to a device for simulating variable lung compliance according to the preamble of the subsequent claim 1.

The present invention aims to achieve a patient simulator that allows for a change in the compliance of the lungs, i.e. the resistance offered by the lungs when ventilated (artificial respiration). This provides an opportunity for practicing diagnosis and treatment of a respiratory problem.

Lung compliance is defined as: "the pulmonary volume change per unit pressure change. While this clearly not a complete description of the pressure-volume properties of the lung, it is nevertheless useful in practice as a measure of the comparative stiffness of the lung. The stiffer the lung, the less is the compliance. Compliance is reduced by diseases which cause an accumulation of fibrous tissue in the lung or by oedema in the alveolar spaces. It is increased in pulmonary emphysema and also with age, probably because of alterations in the elastic tissue in both cases"—www.biology-online.org. The compliance of a human lung is typically not linear.

It is a great advantage for medical practitioners, paramedics and other health care persons to practice resuscitation also on cases where the patient has reduced compliance due to one of the diseases that causes such a defect.

Leardal Medical AS has suggested a manikin with a lung simulator that has the ability to simulate a change in the lung compliance. In WO 2005/032327 this device was described in an embodiment where the lung or lungs where placed between two plates in the chest. The spacing between the plates or their resistance against moving apart could be altered, so that it became more difficult to inflate the lungs. The lower plate was fixed while the upper plate was movable. The upper was forced up when the lung was inflated through artificial respiration, simulating lifting of the chest. The normal resistance against this ventilation was caused by the chest skin stretching when the chest lifted. In order to initiate an increase in the inflexibility of the lungs an actuator was activated, which pulled the upper chest plate down towards the lower plate. This applied a pressure to the lung sack and made it more difficult for the user to blow air into the lungs. The actuator included a pneumatically operated mechanism or an electromechanical mechanism, while the strap was an elastic strap, band or a tension spring.

Although this device gave the desired results it turned out to be fairly complicated, involving several parts. It was also difficult to set the desired amount of compliance by the actuator.

There are also known some other devices that can be used to set a specific lung compliance:

U.S. Pat. No. 3,736,362, which also belongs to the same applicant shows the use of two springs to increase the compliance. The pre-tensioning of the springs may be adjusted. However, there are shown no means of adjustment and the adjustment would most likely have to be done by replacing the springs or some sort of manual adjustment. This means that adjustment of the compliance takes quite some time and would in practice be done very infrequently.

DE 3049583 shows a set of springs where the tensioning of the springs can be adjusted to vary the compliance. This adjustment also has to be done manually by turning a set of nuts. It is also very difficult to set the compliance to a reasonably accurate value.

US Re29317 describes the use of an adjustable spring to vary compliance. In this case the adjustment is done by sliding a block, to which one end of the spring is fixed, along a rail. The block is fixed to the rail by a screw. This adjustment also has to be done manually and it is also here very difficult to set a predetermined value.

U.S. Pat. No. 4,430,893 shows in principle the same as US Re29317, and it involves the same disadvantages.

The above prior art devices also have yet another common disadvantage. There is no direct correlation between the actual compliance and a desired compliance. This means that is a computer is connected to the manikin, the computer has none or very limited ability to know which compliance the lung is set to. The result is that the compliance cannot or in a very limited way be taken into account when the physical condition of the manikin is determined. This means that since the computer does not have an accurate value for the actual compliance it cannot give correct feedback on the performance of the user. It is therefore an additional object for the present invention to provide a means for setting the compliance to one of a number of values that the computer will have information about and can take into account when giving feedback to the user.

Some prior art devices does not only vary the compliance of the lung, but also the available volume. This is highly undesirable since it does not give the same effect as on a real patient, where the lung volume effectively stays the same even if the compliance varies.

It is accordingly an object of the present invention to provide a device of the initially stated type, which is easy to adjust into different compliances and gives an accurate and recognizable compliance value. The value should be independent of the temperature of the patient simulator or the surroundings. The patent simulator can be used both indoors and outdoors, so that the temperature may vary by several tens of degrees Celsius.

Moreover, the compliance value should be independent of the material chosen for the lung. It should be possible to replace the lung with another lung without having to make any adjustments on the device to get correct compliance values.

This is achieved by a device for simulating variable lung compliance, comprising a structure having two main components between which an artificial lung is situated, the main components being adapted to be moved away from each other by the lung when the lung is inflated and are adapted to move towards one another to force air out of the lung in an exhalation phase; and a biasing means acting between the two main parts to provide a force that acts to move the two main parts towards one another, wherein the biasing means comprises at least one spring, which is selectively attachable between the two main parts upon actuation by a spring holding mechanism.

Preferably, the holding mechanism comprises a spring gripping means and an actuator adapted to move the spring gripping means between a spring gripping position and a spring releasing position. This makes it possible to remotely adjust the compliance values.

If the actuator is a solenoid, a simple and compact device is achieved.

If the biasing means comprises at least two springs that are selectively attachable between the two main parts upon actuation by a respective spring holding mechanism and the springs have different elasticity coefficients, the option of choosing between multiple compliance values is provided.

If the device further comprises a basic biasing means, which is constantly coupled between the two main parts a basic lung compliance, simulating a normal lung is provided.

The two main parts are preferably hingedly coupled and that the at least one spring is situated opposite of the hinge. This results in a simple and compact device and good predictability of the compliance values.

If the two main parts comprises a pair of generally plate shaped components it is easy to accommodate the artificial lung between the plates.

In a preferred embodiment the device comprises a computer containing a table of compliance values and corresponding sets of springs, which in combination gives each compliance value, the computer being adapted to receive a desired compliance value, on the basis of the table, decide which combination of springs to be activated, and to initiate a signal to the spring holding mechanisms of those springs, so that the springs that in combination gives the desired compliance value are coupled between the two main parts. This way the instructor or a computer program can enter a desired compliance value without having to pay attention to the multitude of possible combinations of active springs.

If the spring gripping means is a hook with an inclined face facing the spring and an undercut adjacent the inclined face, and the inclined face being adapted to abut a loop on the spring and guide the loop into the undercut, so that the loop is caught in the undercut, a simple means of automatically connecting the spring between the two main components is provided.

The invention will now be described in more detail referring to the accompanying drawings, in which:

FIG. 1 shows a perspective view of a preferred embodiment of the present invention, FIG. 2 shows a partial longitudinal section through the device of FIG. 1 with a spring engaged, FIG. 3 shows a partial longitudinal section through the device of FIG. 1 with a spring disengaged, and FIGS. 4-7 show diagrams of pressure vs. volume for a device including a set of two springs in which none, one or both springs are actuated.

FIG. 1 shows a unit embodying a preferred embodiment of the present invention. The unit is intended for placement within the chest of a resuscitation practice manikin, like the manikin made by Laerdal Medical AS and sold under the trademark SimMan®. However, the unit can also be included in other types of resuscitation practice equipment.

When directional words such as "lower" and "upper" are used in the following, they are intended to denote the orientation or situation of part as they are shown in the drawings, which is also the usual orientation when the device is in use. However, it should be noted that the orientation of the device may deviate from what is shown in the drawings, even when it is in use.

The unit comprises an artificial lung 1, which is preferably made of a plastic sheet material, as is commonly known in the field. The lung is placed in a lung holding structure 2, which has two main components. The first main component is a lower fixture 3 and the second main component is an upper pressing plate 4. The fixture and the pressing plate are hingedly coupled to one another by a hinge 5. The lung 1 is placed between the main components 3, 4, so that when air is forced into the lung 1 and thereby expanding the lung 1, the pressing plate 4 is lifted from the fixture 3 and rotated about the hinge 5. The hinge 5 may be of any type that allows the pressing plate 4 to swing relative to the fixture 3, but in the present embodiment is comprises a hinge pin 6 that is received at respective ends thereof in pin holes 7 formed in a respective post 8 projecting perpendicularly from the fixture 3, and a pair of eyelets 9 projecting from the pressing plate 4.

In order to expel air from the lung 1 during a simulated exhalation phase a biasing means in the form of an elastic band 10 is acting between the pressing plate 4 and the fixture 3, thereby providing a biasing force that will act to move the pressing plate 4 towards the fixture 3. The pressing plate 4 has a hook 11 and the fixture has a hook 12 to receive a respective end of the elastic band 10. The elastic band 10 may preferably be an endless rubber band. Preferably, an elastic band is provided on each of the two longitudinal sides of the holding structure 2.

At the end of the lung holding structure 2 comprising the hinge 5, the inlet and exit opening of the lung 5 is oriented. An airway resistance valve 13 is attached to the fixture 3 and connected to the opening of the lung 1. An airway tube 14 is connected to the valve 13. When air is forced into the tube, typically from a resuscitation bag or from a person practicing resuscitation, the air enters the valve 13 and is restricted to a predetermined degree corresponding to the amount of resistance in a human airway. The restriction of the valve can be adjusted to simulate normal resistance or pathological resistance. A pressure tube 15 is also connected to the valve 13. Through this tube 15 the pressure in the lung may be monitored. The valve 13 is of a per se known design and will not be described in further detail.

At the end of the lung holding structure 2 opposite of the hinge 5, is provided a compliance setting means 16. The compliance setting means comprises a pair of springs 17, 18, preferably helix springs, which are attached to the edge of the pressing plate 4. The attachment may be made in any suitable way, but in the preferred embodiment the attachment is a pin 19 projecting from the edge of the pressing plate 4, over which a loop 20 on the spring 17, 18 is slipped, and ring 21 circumscribing the pin 19, to prevent the loop 20 from slipping off the pin 19. The look may easily be slipped over the pin 19 by tilting the spring towards the hinge end of the structure and thread the loop 20 between the ring 21 and the pin 19. On its upper side the pin has a notch 31 (see FIG. 2), to further prevent the spring from disengaging the pin.

At the opposite end the springs 17, 18 may be selectively attached to a spring holding mechanism 22, 32. The spring holding mechanism 22, 32 is best shown in FIGS. 2 and 3. FIG. 2 shows a partial longitudinal section through a spring holding mechanism in a state where the spring 17, 18 is engaged. The mechanism comprises a hook 23, which is shaped with an undercut 24, forming a shoulder 25, under which a loop 26 on the spring 17, 18 may be received. On the top side of the shoulder 25, opposite the undercut, the hook 23 has an inclined face 27. The hook is coupled to a solenoid 28, which is adapted to slide the hook into the position shown in FIG. 2. A spring 29 is adapted to return the hook into the position shown in FIG. 3, when the solenoid is de-energized. The hook is slidable on a sliding face 30 between the two positions shown.

The elasticity of the elastic bands 10 are adapted so that when only the elastic bands act between the pressing plate 4 and the fixture 3, and the springs 17, 18 are disengage, the lung will have the compliance of a normal healthy lung. To simulate increased compliance one or both of the springs 17, 18 will be engaged by the hook 23 of the holding mechanism 22, 32. To engage a spring 17, 18, the solenoid 28 is energized to draw and hold the hook against the force of the spring 29 to a position where the shoulder 25 is immediately below the spring 17, 18, i.e. the position shown in FIG. 2. Then the pressing plate 4 is lowered due to exhalation from the lung 1, the loop 26 of the spring 17, 18 will strike against the inclined face 27, slide down to the tip of the shoulder 25, slip into the undercut 24 and come to rest against the underside of the shoulder 25. The underside of the shoulder is slightly inclined downwards towards the tip of the shoulder 25, so that the loop cannot easily come free from the undercut 24.

When the pressing plate 4 is moved upwards again due to inflation of the lung, the spring will act with its force against this movement, thereby increasing the resistance against inflation of the lung, i.e. we have an increased compliance.

When it is desirable to reduce the compliance, the solenoid is disengaged so that it is allowed to move into the position shown in FIG. 4, where the shoulder 25 is no longer situated below the spring 17, 18. This allows the loop 26 of the spring to slip out of the undercut 24 and hence come free from the engagement with the hook 23. Thereby, the spring cannot restrict the movement of the pressing plate 4.

The device of the present invention may have any number of springs 17, 18, only limited by the available space along the edge of the pressing plate 4. In the embodiment shown, the device has two springs, which may have different elasticity coefficients. By engaging either both springs 17, 18, spring 17, spring 18 or none, four different compliance values for the lung may be set. If the manikin has two lungs, one on each side of the chest, each of these lungs may be equipped with a device according to the present invention. It is possible to use springs with different elasticity coefficients for the all the springs in both devices. Hence two devices with two springs each may together give the option of choosing between a total of 16 different compliances.

Preferably, a computer will be used to control the solenoids 28. The computer may contain a table of different compliance values and which combination of springs that corresponds to each value. Setting a specific compliance will then trigger a set of signals to the solenoids which will engage the springs that in combination gives the desired compliance value. The table may look like the theoretical table 1 below, giving volume vs. pressure for different combinations of springs activated or not. This way the pressure may be measured via the hose 15, as stated above and the volume of the lung can be determined by looking up in the table. In the example a measured pressure of 25 mbar means that if spring 2 is activated, the actual volume in the lung will be 325 ml.

TABLE 1

| Pressure (mbar) | Volume (ml) | | | |
| --- | --- | --- | --- | --- |
| | No spring activated | Spring 1 activated | Spring 2 activated | Spring 1 and 2 activated |
| 0.7 | 25 | 10 | 30 | 15 |
| 2 | 50 | 25 | 35 | 50 |
| 4 | 65 | 50 | 70 | 75 |
| 6 | 185 | 100 | 95 | 100 |
| . | . | . | . | . |
| . | . | . | . | . |
| . | . | . | . | . |
| 25 | 575 | 395 | 325 | 310 |
| 30 | 630 | 440 | 390 | 360 |
| 37 | 695 | 490 | 450 | 430 |
| 43 | 735 | 535 | 500 | 475 |

FIGS. 4-7 show actual values of pressure vs. volume of a tested set of springs. Each curve represents a specific condition for the "patient". These values will be represented as tables similar to table 1 in the computer.

This means that the set compliance and the actual compliance will always correspond. It is therefore possible to take the compliance into account in the calculations, and the computer can easily determine if the practicing person is giving an optimal treatment to the simulated patient and give feedback to the student on the quality of the CPR. Values significant for the quality of the CPR can also be stored for later review.

It is also possible to assign a specific combination of spring to specific diseases, so that the trainer can set the manikin into simulating a specific disease, which is characterized by a certain degree of compliance, and the computer will energize the solenoids which engage the springs that in combination give this compliance.

A person of skill will envisage other ways of embodying the present invention. It is not necessary to use a hinge connection between the two main parts of the structure as, e.g., a device having a pressure plate which can move in parallel also will function according to the aims of the present invention. It is also possible to use other means for engaging the springs than a solenoid operated hook, e.g. an electro-magnet acting on a permanent magnet attached to the spring. The actuator may also be pneumatic, hydraulic or a screw rotated by an electromotor. Instead of using helix springs to provide increased compliance, it is also possible to use other types of biasing means, like elastic bands, gas springs, volute springs or leaf springs. Consequently, these and other modifications lie within the freedom of the person of skill when exploiting the present invention.

The invention claimed is:

1. A device for simulating variable lung compliance comprising:
   a structure having two main components between which an artificial lung is situated;
   the two main components being adapted to be moved away from each other by the artificial lung when the artificial lung is inflated and adapted to move towards one another to force air out of the artificial lung in an exhalation phase;
   a biasing member selectively attachable between the two main components to provide a force that acts to move the two main components towards one another;
   a holding mechanism comprising a gripper actuatable by an actuator to move the gripper between a gripping position attaching the biasing member to the two main components and a release position disconnecting the biasing member from the two main components; and
   wherein the gripper comprises a hook with an inclined face facing a spring and an undercut adjacent to the inclined face, and the inclined face is adapted to abut a loop on the biasing member and guide the loop into the undercut so that the loop is caught in the undercut.

2. The device of claim 1, wherein the holding mechanism comprises an actuator to move the gripper between the gripping position and the release position.

3. The device of claim 2, wherein the actuator is a solenoid.

4. The device of claim 1, further comprising a second biasing member selectively attachable between the two main components upon actuation of a second holding mechanism, the biasing members having different elasticity coefficients.

5. The device of claim 4, further comprising a computer to receive a desired compliance value and to initiate a signal to actuate the holding mechanism and the second holding mechanism to achieve the desired compliance value.

6. The device of claim 1, further comprising a basic biasing member constantly coupled between the two main components to provide a basic lung compliance, simulating a normal lung.

7. The device of claim 6, wherein the basic biasing member comprises at least one of a spring and an elastic band.

8. The device of claim 1, wherein the two main components are hingedly coupled and the biasing member is situated opposite of a hinge.

9. The device of claim 1, wherein the two main components comprise a pair of generally plate shaped components.

10. The device of claim 1, wherein the biasing member is one of a spring or an elastic band.

\* \* \* \* \*